(12) United States Patent
Shekalim et al.

(10) Patent No.: US 6,971,813 B2
(45) Date of Patent: Dec. 6, 2005

(54) CONTACT COATING OF PROSTHESES

(75) Inventors: Avraham Shekalim, Nesher (IL); Eyal Teichman, Hod-Hasharon (IL)

(73) Assignee: Labcoat, Ltd., (IE)

( * ) Notice: Subject to any disclaimer, the term of this patent is extended or adjusted under 35 U.S.C. 154(b) by 164 days.

(21) Appl. No.: 10/256,755

(22) Filed: Sep. 27, 2002

(65) Prior Publication Data
US 2004/0062592 A1    Apr. 1, 2004

(51) Int. Cl.⁷ .................. B05C 17/00; B05C 1/00; A46B 15/00
(52) U.S. Cl. .................. 401/208; 401/9; 118/227; 118/244; 118/258
(58) Field of Search ................. 401/218, 208, 401/197, 198, 261, 121, 119, 9, 10, 11, 219, 401/220; 427/2.25, 2.24; 118/218, 224, 227, 118/228, 232, 233, 244, 258; 138/99

(56) References Cited

U.S. PATENT DOCUMENTS

| | | | |
|---|---|---|---|
| 2,464,040 A * | 3/1949 | Huebner ................. | 492/25 |
| 5,298,276 A * | 3/1994 | Jayaraman ............... | 427/2.25 |
| 5,763,330 A | 6/1998 | Bertolucci et al. | |
| 5,773,081 A | 6/1998 | Williamitis et al. | |
| 5,925,259 A | 7/1999 | Biebuyck et al. | |
| 6,190,077 B1 * | 2/2001 | Newson et al. ........... | 401/192 |
| 6,352,768 B1 | 3/2002 | Hseih et al. | |
| 6,355,058 B1 * | 3/2002 | Pacetti et al. ........... | 427/2.25 X |
| 6,413,318 B2 | 7/2002 | Yoo et al. | |
| 6,428,853 B1 | 8/2002 | Eriksson | |

FOREIGN PATENT DOCUMENTS

WO    02/14078 A2    2/2002

OTHER PUBLICATIONS

Adler, L.M., et al., "Analysis of exposure times and dose escalation of paclitaxel in ovarian cancer cell lines," *Cancer* 74(7):1891-1898, Abstract only, 1994.

"Basic Theory: How does transfer pad printing work?," http://www.itwtranstech.com/pages/how.html, Trans Tech America Inc., 2002.

Farb, Andrew, "Comparative Pathology of Drug Eluting Stents: Insights Into Effectiveness and Toxicity from the Animal Lab," Presentation from CRF Drug-Eluting Stent Symposium, http://tctmd.com/expert-presentations, 2002.

Hiatt, Bonnie L. et al., "Drug-Eluting Stents for Prevention of Restenosis: In Quest for the Holy Grail," *Catheterization and Cardiovascular Interventions* 55:409-417, 2002.

(Continued)

*Primary Examiner*—David J. Walczak
(74) *Attorney, Agent, or Firm*—Kudirka & Jobse, LLP

(57) ABSTRACT

A method and apparatus for coating prostheses via contact patterning with an applicator. Applicators can include rollers, tampons, and ribbons. Coating materials include a variety of substances including polymers and therapeutic agents.

10 Claims, 9 Drawing Sheets

OTHER PUBLICATIONS

Kalinowski, M., et al., "Paclitaxel inhibits proliferation of cell lines responsible for metal stent obstruction: Possible topical application in malignant bile duct obstructions," *Invest Radiol* 37(7):399-404, Abstract only, 2002.

Kandzari, David E., et al., "Highlights from the American Heart Association Annual Scientific Sessions 2001: Nov. 11-14, 2001," *American Heart Journal* 143(2):217-228, 2002.

Liebmann, J.E., et al., "Cytotoxic studies of paclitaxel (Taxol) in human tumor cell lines," *Br J Cancer* 68(6):1104-1109, Abstract only, 1993.

Regar, E., et al., "Stent development and local drug delivery,"*Br Med Bull* 59:227-248, Abstract only, 2001.

Taxol Quanam Data and the SCORE study, Grube E. (the effect of taxol on the edges of the stent and dose response screening) 6-7. ISET 2002 Miami Beach, Mar. 19-23, 2002.

Sirolimus: Pre-clinical studies—Evaluatin of dosing, efficacy and toxicity. Andrew J. and Carter D.O., TCT Sep. 2001.

* cited by examiner

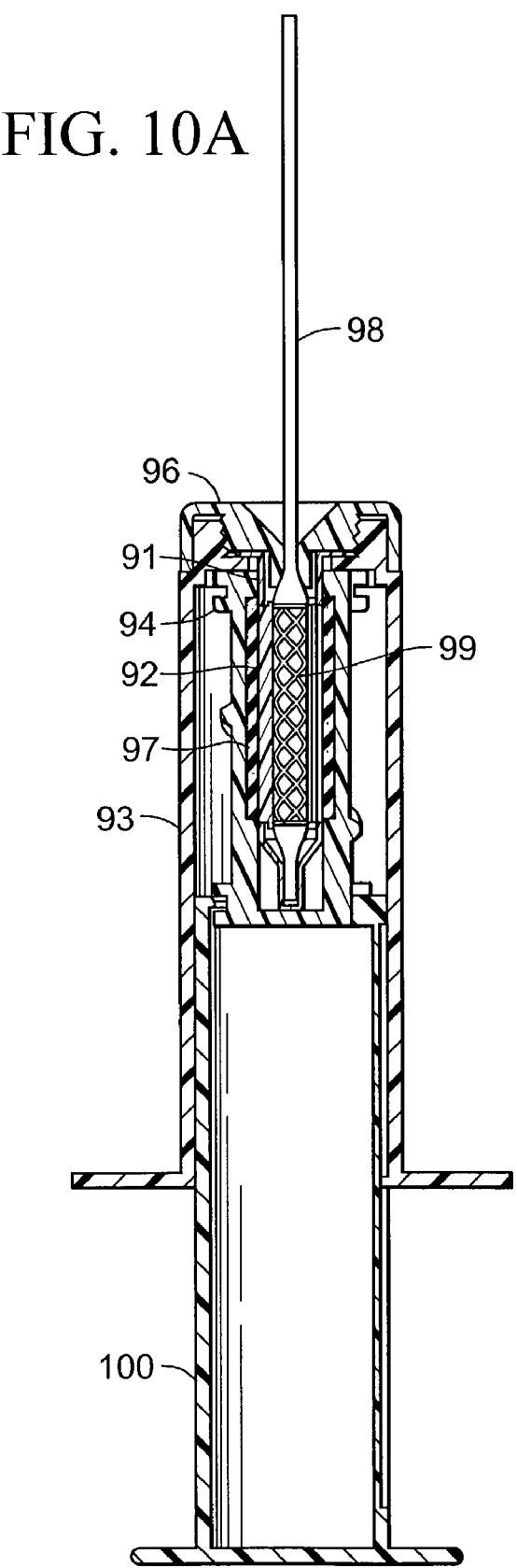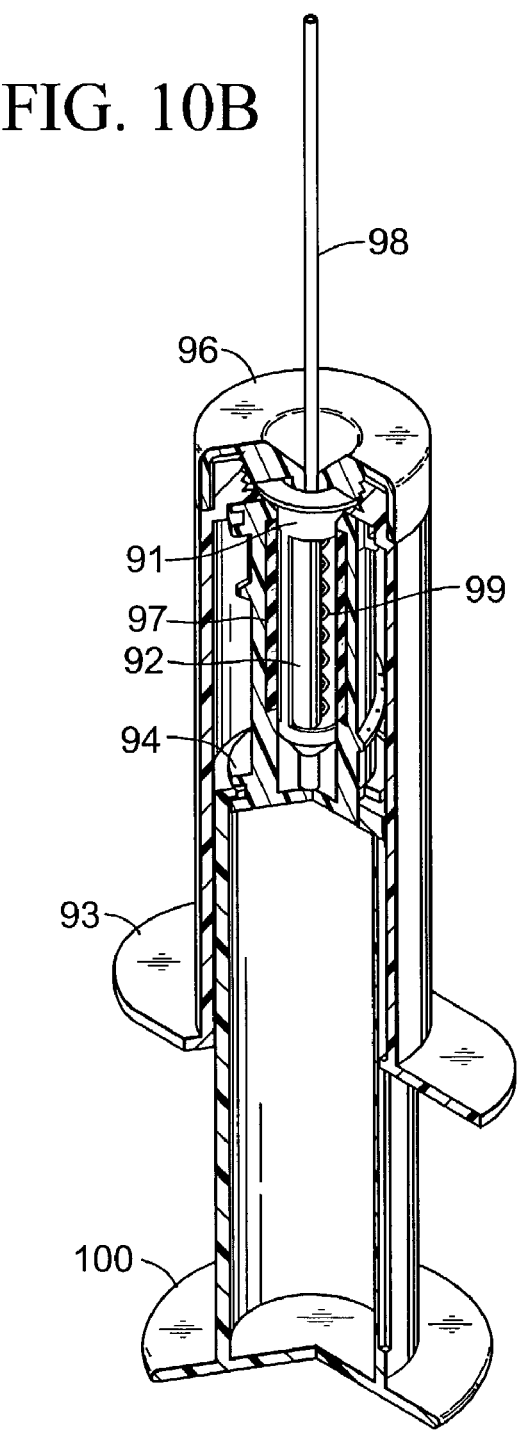

CONTACT COATING OF PROSTHESES

DESCRIPTION OF THE INVENTION

1. Field of the Invention

This invention relates generally to implantable devices or prostheses. More particularly, the invention is directed to an apparatus and method for coating a prosthesis using contact printing.

2. Definitions

The term "prosthesis" refers to any one of many medical coating applications including but not limited to coronary stents, peripheral vascular stents; abdominal aortic aneurysm (AAA) devices, biliary stents and catheters, TIPS catheters and stents, vena cava filters, vascular filters and distal support devices and emboli filter/entrapment aids, vascular grafts and stent grafts, gastro enteral tubes/stents, gastra enteral and vascular anastomotic devices, urinary catheters and stents, surgical and wound drainings, radioactive needles and other indwelling metal implants, bronchial tubes and stents, vascular coils, vascular protection devices, tissue and mechanical prosthetic heart valves and rings, arterial-venous shunts, AV access grafts, surgical tampons, dental implants, CSF shunts, pacemaker electrodes and leads, suture material, wound healing, tissue closure devices including wires, staplers, surgical clips etc., IUDs and associated pregnancy control devices, ocular implants, timponoplasty implants, hearing aids including cochlear implants, implantable pumps (like insulin pumps), implantable cameras and other diagnostic devices, drug delivery capsules, left ventricular assist devices (LVADs) and other implantable heart support and vascular systems, indwelling vascular access catheters and associated devices (like ports), maxilo fascial implants, orthopedic implants (joint replacement, trauma management and spine surgery devices), implantable devices for plastic and cosmetic surgery, implantable meshes (such as for hernia or for uro-vaginal repair, brain disorders, and gastrointestinal ailments).

The term "contact pattern" or "contact patterning" refers to utilizing transfer pad printing principles known in the art of contact printing to coat prostheses. Transfer pad printing includes open inkwell pad printing, sealed ink cup pad printing, and rotary gravure pad printing. In an example of open inkwell pad printing, a spatula scoops ink out of an inkwell and over an entire cliché plate surface with a doctor blade lifted off the surface. The pad slide moves to the right as the doctor blade removes excess ink from the cliché. A transfer pad or tampon is then pressed against the inked plate and lifted. As the transfer pad moves left toward the object to be printed, new ink is deposited onto the plate. With the new image now slightly tacky, the pad descends to the part, leaves the imprint, and the process is then repeated. In an example of the sealed ink cup positioned over the etched area of a cliché plate. The cliché then moves forward with the hardened metal lip of the cup, doctoring the excess ink off the image area. The pad then descends onto the exposed, inked image. A remaining ink is retained in the cup. The pad picks up the image from the plate which then moves back under the sealed ink cup. The pad pushes downward onto the part to be printed and releases the entire image. At the same time, the cliché is being exposed to ink inside the cup, ready to repeat the cycle. In an example of the rotary pad printing process, ink is first picked up by a cliché drum, which is analogous to the plate in the open ink well printing process. The drum turns to deposit the inked image onto a silicone roller, which acts as the transfer pad. The silicone roller then turns and is met by the part to be printed. Because of the physical capabilities of continuously rotating drums, the rotary process is easily adapted to high-speed applications.

The term "applicator" refers to any device which provides contact coating of a prosthesis known in the art of contact printing. Applicators can include rollers, tampons, ribbons, cliché drums, plates, and other means known in the art.

The term "coating material" refers to any liquid or semi-liquid material chosen from polymers, therapeutic agents, and thin films. The coating materials which can be used in conjunction with the present invention are any desired, suitable substances. In some embodiments, the coating materials comprise therapeutic agents, applied to the medical devices alone or in combination with solvents in which the therapeutic agents are at least partially soluble or dispersible or emulsified, and/or in combination with polymeric materials as solutions, dispersions, suspensions, latices, etc. The terms "therapeutic agents" and "drugs" are used interchangeably herein and include pharmaceutically active compounds, nucleic acids with and without carrier vectors such as lipids, compacting agents (such as histones), virus, polymers, proteins, and the like, with or without targeting sequences. The coating may provide for controlled release, which includes long-term or sustained release, of a bioactive material. Specific examples of therapeutic or bioactive agents used in conjunction with the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. For example, biologically active solutes include anti-thrombogenic agents such as heparin, heparin derivatives, urokinase, and PPACK (dextrophenylalanine proline arginine chloromethylketone); prostaglandins, prostacyclins/prostacyclin analogs; antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflamatory agents such as dexamethasone, prednisolone, corticosterone, budesonide, estrogen, sulfasalazine, acetyl salicylic acid, and mesalamine, lipoxygenase inhibitors; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, colchicine, epothilones, endostatin, angiostatin, Squalamine, and thymidine kinase inhibitors; L-arginine; antimicrobials such astriclosan, cephalosporins, aminoglycosides, and nitorfuirantoin; anesthetic agents such as lidocaine, bupivacaine, and ropivacaine; nitric oxide (NO) donors such as lisidomine, molsidomine, NO-protein adducts, NO-polysaccharide adducts, polymeric or oligomeric NO adducts or chemical complexes; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; interleukins, interferons, and free radical scavengers; vascular cell growth promoters such as growth factors, growth factor receptor antagonists, transcriptional activators, and translational promoters; vascular cell growth inhibitors such as growth factor inhibitors (e.g., PDGF inhibitor—Trapidil), growth factor receptor antagonists, transcriptional repressors, translational repressors, replication inhibitors, inhibitory antibodies, antibodies directed against growth factors, bifinctional molecules consisting of a growth factor and a cytotoxin, bifinctional molecules consisting of an antibody and a cytotoxin; Tyrosine kinase inhibitors, chymase inhibitors, e.g., Tranilast, ACE inhibitors, e.g., Enalapril, MMP inhibitors, (e.g., Ilomastat, Metastat), GP IIb/IIIa inhibitors (e.g., Intergrilin, abciximab), seratonin antagonist, and 5-HT uptake inhibitors; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof; and beta blockers. These and other compounds may be added to a coating solution, including a coating solution that includes a polymer, using similar methods and routinely tested as set forth in the specification. Any modifications are routinely made by one skilled in the art. Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be incorporated into the polymer coating, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor .alpha. and beta., platelet-derived endothelial growth factor, platelet-derived growth factor, tumor necrosis factor .alpha., hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing anupstream or downstream effect of a BMP can be provided. Such molecules include any of the "hedgehog" proteins, or the DNA's encoding them. Coating materials other than therapeutic agents include, for example, polymeric materials, sugars, waxes, and fats, applied alone or in combination with therapeutic agents, and monomers that are cross-linked or polymerized. Such coating materials are applied in the form of, for example, powders, solutions, dispersions, suspensions, and/or emulsions of one or more polymers, optionally in aqueous and/or organic solvents and combinations thereof or optionally as liquid melts including no solvents. When used with therapeutic agents, the polymeric materials are optionally applied simultaneously with, or in sequence to (either before or after), the therapeutic agents. Such polymeric materials employed as, for example, primer layers for enhancing subsequent coating applications (e.g., application of alkanethiols or sulfhydryl-group containing coating solutions to gold-plated devices to enhance adhesion of subsequent layers), layers to control the release of therapeutic agents (e.g., barrier diffusion polymers to sustain the release of therapeutic agents, such as hydrophobic polymers; thermal responsive polymers; pH-responsive polymers such as cellulose acetate phthalate or acrylate-based polymers, hydroxypropyl methylcellulose phthalate, and polyvinyl acetate phthalate), protective layers for underlying drug layers (e.g., impermeable sealant polymers such as ethylcellulose), biodegradable layers, biocompatible layers (e.g., layers comprising albumin or heparin as blood compatible biopolymers, with or without other hydrophilic biocompatible materials of synthetic or natural origin such as dextrans, cyclodextrins, polyethylene oxide, and polyvinyl pyrrolidone), layers to facilitate device delivery (e.g., hydrophilic polymers, such as polyvinyl pyrrolidone, polyvinyl alcohol, polyalkylene gylcol (i.e., for example, polyethylene glycol), or acrylate-based polymer/copolymer compositions to provide lubricious hydrophilic surfaces), drug matrix layers (i.e., layers that adhere to the medical device and have therapeutic agent incorporated therein or thereon for subsequent release into the body), and epoxies. When used as a drug matrix layer for localized drug delivery, the polymer coatings of the present invention comprise any material capable of absorbing, adsorbing, entrapping, or otherwise holding the therapeutic agent to be delivered. The material is, for example, hydrophilic, hydrophobic, and/or biodegradable, and is preferably selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyurea, polyacrylate, polyacrylic acid and copolymers, polyorthoesters, polyanhydrides such as maleic anhydride, polycarbonates, polyethylene, polypropylenes, polylatic acids, polystyrene, natural and synthetic rubbers and elastomers such as polyisobutylene, polyisoprene, polybutadiene, including elastomeric copolymers, such as Kraton®., styrene-isobutylene-styrene (SIBS) copolymers; polyglycolic acids, polycaprolactones, polyhydroxybutyrate valerates, polyacrylamides, polyethers, polysaccharides such as cellulose, starch, dextran and alginates; polypeptides and proteins including gelatin, collagen, albumin, fibrin; copolymers of vinyl monomers such as ethylene vinyl acetate (EVA), polyvinyl ethers, polyvinyl aromatics; other materials such as cyclodextrins, hyaluronic acid and phosphoryicholines; and mixtures and copolymers thereof. Coatings from polymer dispersions such as polyurethane dispersions (BAYHDROL, etc.) and acrylic latex dispersions are also within the scope of the present invention. Polymers can include polyurethanes; polyacrylic acid, and aqueous coating compositions comprising an aqueous dispersion or emulsion of a polymer having organic acid functional groups and a polyfunctional crosslinking agent having functional groups capable of reacting with organic acid groups. The release rate of drugs from drug matrix layers is largely controlled, for example, by variations in the polymer structure and formulation, the difflusion coefficient of the matrix, the solvent composition, the ratio of drug to polymer, potential chemical reactions and interactions between drug and polymer, the thickness of the drug adhesion layers and any barrier layers, and the process parameters, e.g., drying, etc. The coating(s) applied by the methods and apparatuses of the present invention may allow for a controlled release rate of a coating substance with the controlled release rate including both long-term and/or sustained release. Additionally, a coating substance may include suspension particles, e.g., a powder. For example, the suspension particles may be fused to the surface of the prosthesis by a coating solution.

The coatings of the present invention are applied such that they result in a suitable thickness, depending on the coating material and the purpose for which the coating(s) is applied. As an example, coatings applied for localized drug delivery are typically applied to a thickness of 1 to 30 microns, or 2 to 20 microns. Very thin coatings, e.g., of about 100 angstroms., and much thicker coatings, e.g., more than 30 microns, are also possible. It is also within the scope of the present invention to apply multiple layers of the same or different coating materials, which may perform identical or different functions (e.g., to provide for biocompatibility, to control drug release, etc.).

The term "sponge cartridge" refers to any absorbent material capable of absorbing and delivering coating material to an applicator. The absorbent material can be mounted on a member for handling purposes. The absorbent material can be any sponge known in the art of contact printing.

It is noted that, as used in this specification and the appended claims, the singular forms "a," "an," and "the" include plural referents unless expressly and unequivocally limited to one referent. Thus for example, reference to "an applicator" includes two or more applicators, but "n is an integer from 1 to 60" means that n is one integer because that is limited to one integer. Also noted that as used herein, the term "polymer" is meant to refer to oligomers, homopolymers, and copolymers.

For the purposes of this specification and appended claims, unless otherwise indicated, all numbers expressing quantities of ingredients or percentages or proportions of other materials, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

BACKGROUND OF THE INVENTION

Prosthetic devices are artificial devices used to replace or strengthen a particular part of the human body. Various prosthetic devices are available, such as joint replacement prosthesis, stent prosthesis and vascular graft prosthesis. When implanting a prosthesis, such as a stent prosthesis described in greater detail herein, it is desireable that the prosthesis closely assimilate the characteristics of the tissue or bone that the prosthesis is designed to repair or replace. To this end, many attempts have been made to improve biocompatible and mechanical properties of prosthetic devices. Also, it can be desirable to topically medicate the area where the prosthetic has been implanted.

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the vessel wall. The balloon is deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an expandable intraluminal prosthesis, one example of which includes a stent, is implanted in the lumen to maintain the vascular patency.

Percutaneous endovascular prosthetic stents were conceived in the late 1970's as a way to prevent both acute occlusion and late restenosis after catheter intervention, but initial clinical results of coronary stenting in 1987 were plagued by high (>20%) acute and subacute thrombosis and were restricted to use as "bailout" for threatened or acute vessel closure. In recent years, stent outcomes have improved progressively with better placement techniques and in 1995, an estimated 700,000 stents were implanted world-wide.

Stents are scaffoldings, usually cylindrical or tubular in shape, which function to physically hold open and, if desired, to expand the wall of the passageway. Typically stents are capable of being compressed for insertion through small cavities via small catheters, and expanded to a larger diameter once at the desired location.

To treat the damaged vasculature tissue and assist prevention of thrombosis and restenosis, there is a need for administrating therapeutic substances to the treatment site. For example, anticoagulants, antiplatelets and cytostatic agents are commonly used to prevent thrombosis of the coronary lumen, to inhibit development of restenosis, and to reduce post-angioplasty proliferation of the vascular tissue, respectively. To provide an efficacious concentration to the treated site, systemic administration of such medication often produces adverse or toxic side effects for the patient. Local delivery can be a preferred method of treatment in that smaller total levels of medication are administered at a specific site in comparison to larger overall dosages that are applied systemically. Local delivery produces fewer side effects and achieves more effective results.

One commonly applied technique for the local delivery of a drug is through the use of a polymeric carrier coated onto the surface of a stent by applying to a stent body a solution which includes a specified solvent, a specified polymer dissolved in the solvent, and a therapeutic substance dispersed in the blend. The solvent is allowed to evaporate, leaving on the stent surface a coating of the polymer and the therapeutic substance impregnated in the polymer.

Stents sometimes have to be immersed in a coating solution 12 to 15 times or sprayed 20 times to achieve a satisfactory coating. The immersion method of coating a stent, also called dip-coating, entails submerging the entire stent, or an entire section of the stent, in a coating solution. Similarly, spray-coating requires enveloping the entire stent, or an entire section of the stent, in a large cloud of coating material. Disadvantages of dip-coating and spray-coating methods include the inability to control the exact portions of the stent that come in contact with the coating. Another shortcoming of both dip- and spray-coating is the possibility of forming web-like defects by build-up of excess coating material between the stent struts. Web-like defects are most prevalent in stents having tight patterns, for example coronary stents, such that the distance between the struts is very small.

Each of the methods and devices intended for use just prior to implantation, listed above, deposit the coating material onto any and all surfaces that are exposed to the coating. This may result in depositing coating material on surfaces on which the coating is unwanted or undesirable. Further, the coating may crack or break away when the implantable is removed from the implantation apparatus. An example of this would be a stent deployed on a catheter balloon. As the balloon is inflated and the stent is expanded into position, the coating may crack along the interface between the stent and the balloon. These cracks may lead to a breaking away of a portion of the coating from the stent itself. This, in turn, may affect the medicinal effectiveness of the coating, and negatively affect the entire medical procedure.

Another disadvantage of both dip-coating and spray-coating stems from a low-viscosity requirement for the polymer solution in which the stent is dipped or with which the stent is sprayed. A low viscosity coating solution typically require using a low molecular weight carrier or by using a very low concentration of carrier in the coating solution. Thus, both dip-coating and spray-coating methods have imposed limitations in type and concentration of applied carriers.

Accordingly, it is desirable to provide an improved method of applying a coating to a prosthesis. Specifically, it is desirable to provide a method of applying a polymeric coating to a prosthesis which enables control over the portion of the prosthesis which are coated, reduces the incidence of web-like defects due to excess build-up of polymeric material, broadens the field of both the types and the concentrations of carriers which may be used to coat a prosthesis, and allows a prosthesis to be coated with a polymer and a drug at the same time.

The significance of delivering drug-loaded prostheses may offer savings benefit in time and cost. Studies have been conducted to show the importance of delivering the correct drug dose density on coronary stents to prevent restenosis by application of paclitaxel or rapamycin. Kandazari, David E. et al., "Highlights from American Heart Association Annual Scientific Sessions 2001: Nov. 11 to 14," 2001 American Heart Journal 143(2), 217–228, 2002; Hiatt, Bonnie L. et al., "Drug-eluting Stents for Prevention of Restenosis: In Quest for the Holy Grail." Catheterization and Cardiovascular Interventions 55:409–417, 2002; Kalinowski, M. et al., "Paclitaxel Inhibits Proliferation of Cell Lines Responsible For Metal Stent Obstruction: Possible Topical Application In Malignant Bile Duct Obstructions." Investigational Radiology 37(7):399–404, 2002. Other studies have shown how accuracy of dose relate to cytotoxicity of coating drugs. Liebmann, J. E. et al., "Cytotoxic Studies of Paclitaxel (Taxol) In Human Tumor Cell Lines." Br. J. Cancer, 68(6): 1104–9, 1993; Adler, L. M. et al., "Analysis of Exposure Times And Dose Escalation of Paclitaxel In Ovarian Cancer Cell Lines." Cancer, 74(7):1891–8, 1994; Regar, E. et al., "Stent Development and Local Drug Delivery." Br. Med. Bulletin, 59:227–48, 2001.

Accordingly, the desired features of the invention comprise an apparatus and method for coating a prosthesis which avoid the disadvantages of dip-coating and spray coating methods. In addition, coating the prosthesis can be achieved with such control such that the prosthesis can be coated in the operating room prior to insertion of the prosthesis into the patient, thus avoiding coating portions of the prosthesis or prosthesis handling apparatus, such as a catheter, where such a coating is not desirable.

This is achieved by using contact printing techniques which take advantage of known methods of lithography using self-assembled monolayers. Coating desired portions of the prosthesis can be achieved by stamping the prosthesis with a coating that can form a self-assembled monolayer. The surface of the applicator is coated or saturated with the coating and the applicator is placed in contact with the surface of the prosthesis to be coated to transfer the coating from the applicator to the prosthesis surface.

To form a pattern on an arcuate or curved prosthesis surface, including but not limited to a cylindrical surface, the prosthesis can be rolled over a planar applicator or the prosthesis can be rolled over a curved applicator.

SUMMARY OF THE INVENTION

In accordance with the invention, a method of coating comprises (a) obtaining a prosthesis, (b) positioning an applicator in contact with the prosthesis, and (c) translating the applicator over the prosthesis, where translating applies a contact pattern of a coating material on the prosthesis. In one embodiment, the prosthesis is a stent. The stent can comprise a scaffolding network and gapped regions, whereby the applicator contacts the scaffolding network to avoid any significant application to the gapped regions. In one embodiment, the applicator is a roller. In one embodiment, the prosthesis is in contact with an exterior surface of the roller. In another embodiment, the prosthesis is in contact with an interior surface of the roller. In one embodiment, the roller contacts a reservoir comprising the coating material. In one embodiment, a wiper removes excess coating material from the roller prior to contacting the prosthesis. In one embodiment, the roller contacts a sponge comprising the coating material. In one embodiment, the applicator is at least two rollers positioned in contact with the prosthesis. In one embodiment, the applicator is a ribbon spooled around at least two rollers. In one embodiment, the applicator is a tampon. In one embodiment, the tampon contacts a sponge comprising the coating material. In one embodiment, the tampon contacts a cartridge comprising the coating material chosen from polymers, therapeutic agents, or mixtures thereof. In one embodiment, the method further comprises (d) moving the prosthesis in a direction opposite to the movement a applicator. In one embodiment, the coating material comprises materials chosen from polymers, therapeutic agents, or mixtures thereof.

In accordance with the invention, a coating device comprises an applicator, wherein the applicator is adapted to contact patterning a coating material on a prosthesis. In one embodiment, the prosthesis is a stent-catheter system. In one embodiment, the applicator is a roller. In one embodiment, the roller is adapted to repeat the patterning on a surface of the prosthesis. In one embodiment, the roller is in contact with a sponge containing the coating material. In one embodiment, the applicator is a ribbon spooled around two rollers. In one embodiment, the ribbon of the applicator is in contact with a sponge containing the coating material. In one embodiment, the applicator is a tampon. In one embodiment, the tampon is in contact with a sponge containing the coating material.

In accordance with the invention, an applicator for coating comprises a contact printing surface, wherein the surface is adapted to apply a coating material to a prosthesis, and a sponge, the sponge adapted to apply the coating material to the contact printing surface. In one embodiment, the surface is curved and tangentially contacts the prosthesis. In one embodiment, the surface is flat and parallel to the prosthesis.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIG. 9A illustrates a 2-D cut-away view, FIG. 9B illustrates a 3-D cut-away view, and FIG. 9C illustrates a cross-sectional view of the prosthesis and rollers.

FIGS. 10A–10C illustrate a schematic of a prosthesis coating device with a roller embodiment for an applicator during the coating process. FIG. 10A illustrates a 2-D cut-away view, FIG. 10B illustrates a 3-D cut-away view, and FIG. 10C illustrates a cross-sectional view of the prosthesis and rollers.

DESCRIPTION OF THE EMBODIMENTS

Reference will now be made in detail to the present embodiments (exemplary embodiments) of the invention, examples of which are illustrated in the accompanying drawings. Wherever possible, the same reference numbers will be used throughout the drawings to refer to the same or like parts.

In one non-limiting embodiment, liquid or semi-liquid coating materials can be applied to a prosthesis using a roller apparatus and method. One of the advantages of the roller is the ability to synchronize velocity of movement between the roller and the prosthesis. Rotation over the surface of the prosthesis provides substantially uniform pressure and/or forces on the prosthesis, for example, by preloaded springs. Control of the amount of coating material applied provides control for the thickness of coating material applied to the prosthesis by the aid of different approaches such as a wiper, control for the level necessary to supply the roller with sufficient coating material, and high consumption of coating material. The cylindrical shape of the roller can provide a single contact line or point. These features provide for a simple, cheap, and quick operation for coating the prosthesis.

Figure 1:
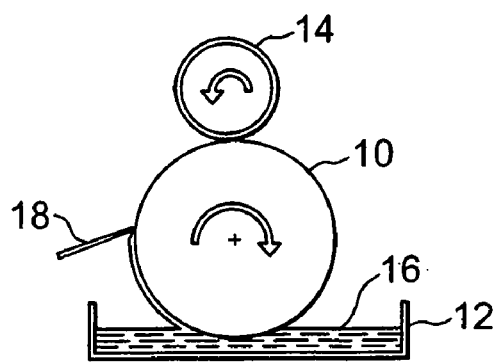
FIG. 1 illustrates a roller embodiment for an applicator with a wiper and coating material tray.

FIG. 1 illustrates an embodiment where a roller 10 which rotates in the clockwise direction, and a cylindrical prosthesis 14, for example a stent, which rotates counterclockwise. Wiper 18 limits the amount of coating material 16 which is transmitted to the surface of prosthesis 14 from reservoir 12 by roller 10. In another embodiment, reservoir 12 can be replaced with a sponge soaked with coating material 16.

In other embodiments the roller can be modified to minimize length of time to coat the desired surfaces of the prosthesis and utilize a minimum of coating material. In one example, two or three rollers can be used to coat the prosthesis. The rollers can move laterally over the surface of the prosthesis or around the prosthesis. Both of these movements of the rollers can be coordinated with movement of the prosthesis. In another example, the prosthesis can be positioned inside the roller and coated. For instance, a hollow cylindrical roller can be used to coat along its interior circumference. The prosthesis can be placed inside the hollow portion of the cylindrical roller and coated by the movement of the roller and/or movement of the prosthesis.

Figure 3:
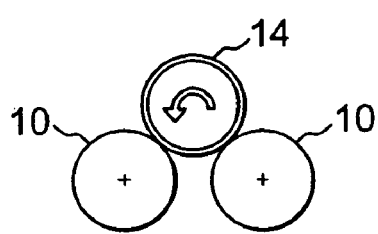
FIG. 3 illustrates a roller embodiment with two rollers as applicator.
Figure 5:
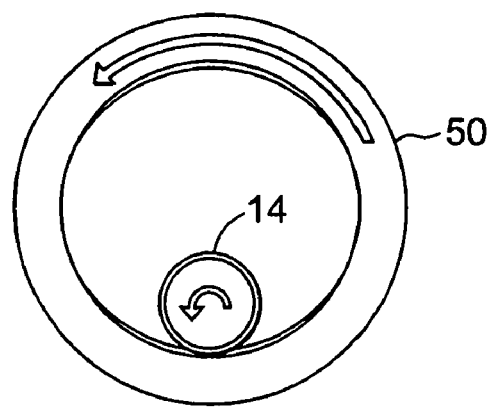
FIG. 5 illustrates a roller embodiment for an applicator where the prosthesis in positioned internally.

FIG. 3 illustrates an embodiment with two rollers 10 which are free to rotate either clockwise or counter-clockwise and prosthesis 14 which rotates counter-clockwise. The use of two rollers 10 decreases the surface area of prosthesis 14 covered by each roller 10. FIG. 5 illustrates an embodiment with a hollow roller 50 which rotates counter-clockwise and a prosthesis 14 positioned on the interior of hollow roller 50. The prosthesis 14 rotates counter-clockwise.

Figure 9A:
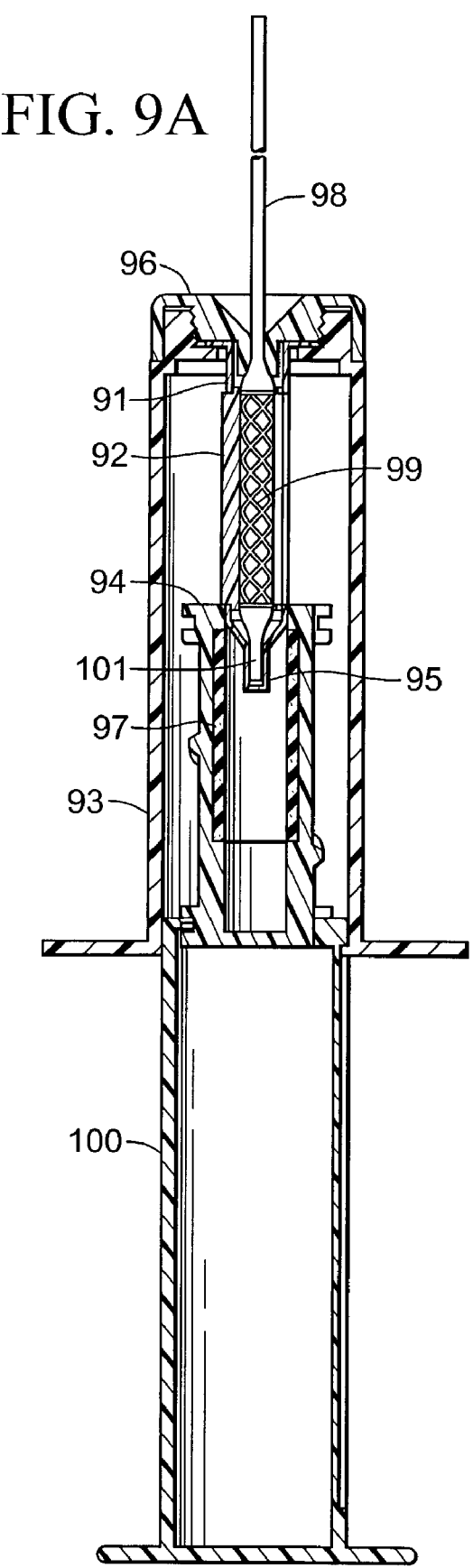
FIGS. 9A–9C illustrate a schematic of a prosthesis coating device with a roller embodiment for an applicator upon insertion of the prosthesis into the coating device.
Figure 9B:
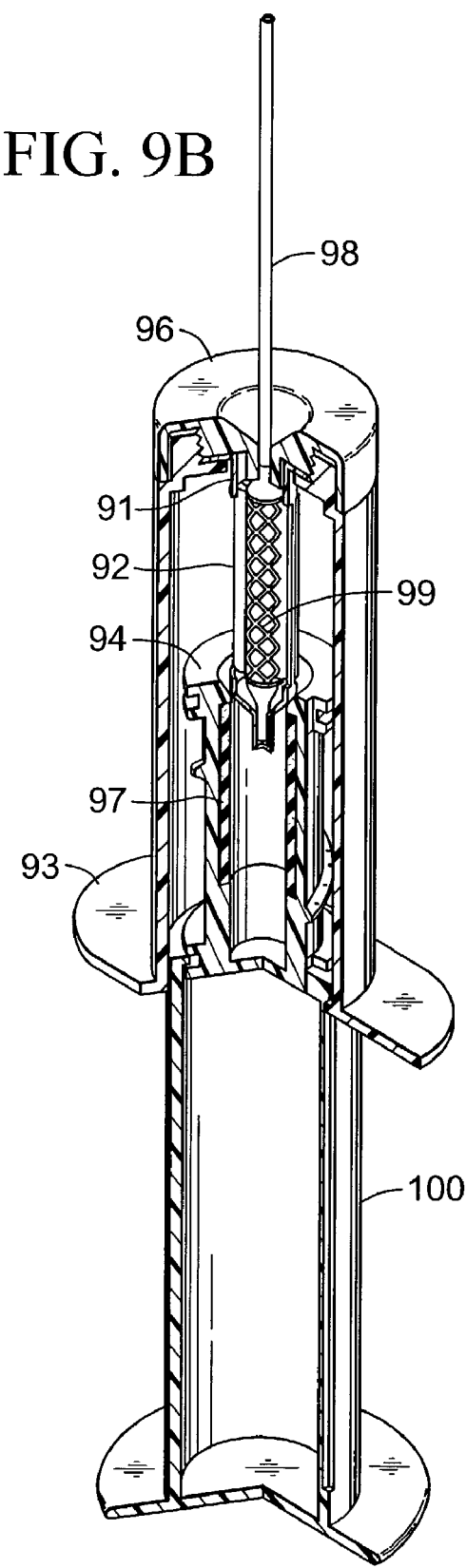
Figure 9C:
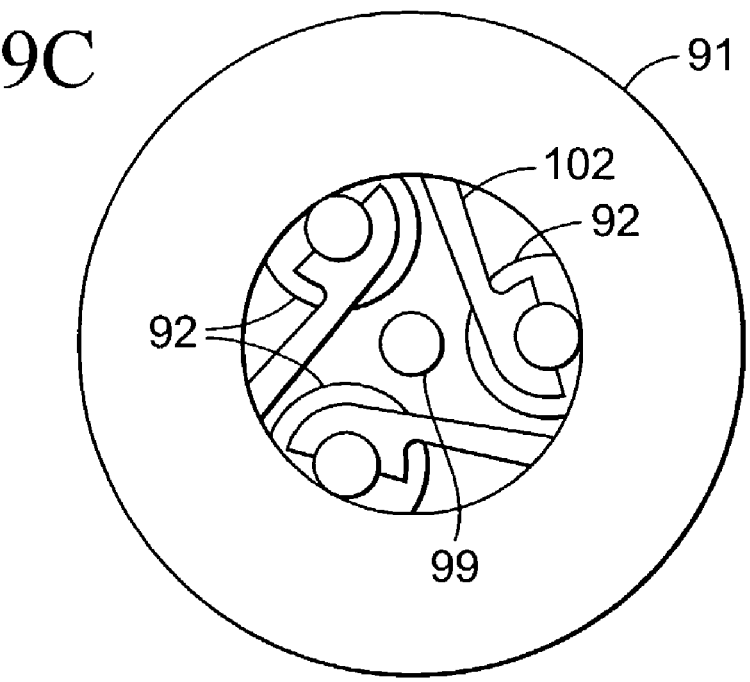

FIGS. 9A–9C illustrate a schematic of a prosthesis coating device with a roller embodiment for an applicator upon insertion of the prosthesis into the coating device. FIG. 9A illustrates a 2-D cut-away view, FIG. 9B illustrates a 3-D cut-away view, and FIG. 9C illustrates a cross-sectional view of the prosthesis and rollers. In this embodiment, the prosthesis is a cylindrical stent 99 mounted on a balloon catheter 98. The balloon catheter 98 and stent 99 are inserted into static housing 93 until the catheter tip 101 is received in rotor cap 95. The catheter 98 and stent 99 are secured into static housing 93 by turning catheter holder 96. In this embodiment, three rollers 92 are prevented from touching the surface of the stent 99 by elastic arms 102 holding the rollers 92 as illustrated in FIG. 9C.

Figure 10C:
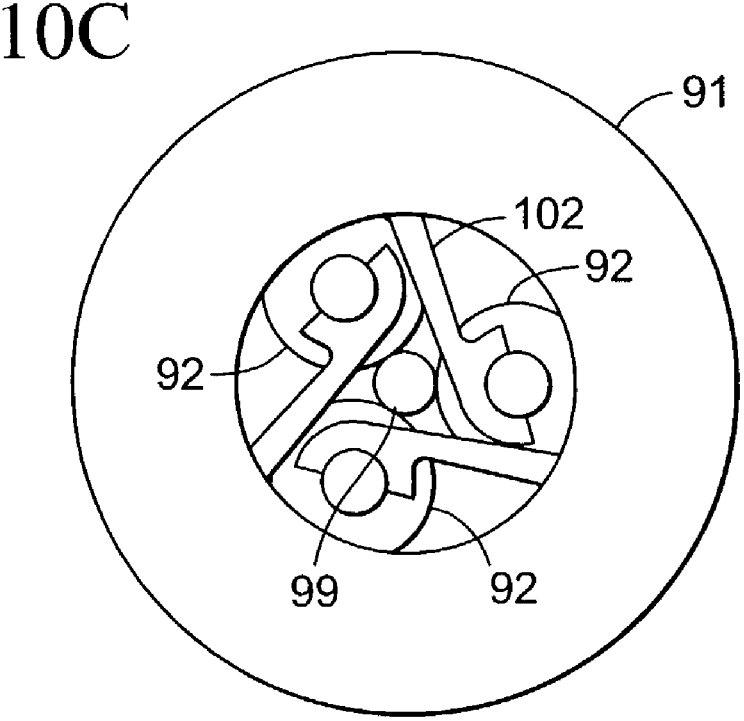

The user then soaks or prepares the sponge cartridge 97 which acts as reservoir for the coating material to be applied to the stent 99. The sponge cartridge 97 is positioned into sponge holder 94. The sponge holder 94 is positioned via pusher 100 into static housing 93 such that it envelops the rollers 92, stent 99 and catheter tip 101, and that sponge cartridge 97 overlaps with rollers 92 as illustrated in FIGS. 10A and 10B. This position pushes the rollers 92 radially inward toward the stent 99 causing the rollers 92 to contact the stent 99 as illustrated in FIG. 10C. The amount of pressure applied by rollers 92 to stent 99 is determined by the shape and elasticity of elastic arms 102 and the elasticity of sponge cartridge 97. Pressure can be between 1.0 gram per square centimeter to 1.0 kilogram per square centimeter. The pressure can be achieve by spring preloading of the roller to the prosthesis while supporting the prosthesis from its other side (the elastic arms 102 can also have some spring properties so they can preload the prosthesis). Alternatively, flexible material (rubber, silicon etc.) can be used as roller material to maintain constant distance between the roller axis and the prosthesis axis (if the distance is lower then the sum of the rollers and prosthesis radius the roller will be preloaded to the prosthesis in pressure that is a function of the material properties). The sponge holder 94 is rotated in the static housing 93 and rotor 91 rotates rollers 92 to apply the coating material over the circumference of the stent 99. The coating material is transferred from the sponge cartridge 97 to the rollers 92 and after half a turn to the surface of stent 99. The coating device can be prevented from recoating via a groove in the static housing 93. In one embodiment, the roller rotation is caused by the operator of pusher 100, sponge cartridge 97 slides over screw-type teeth in the rollers 92 and sponge holder 94 that rotate via the linear movement of the sponge cartridge 97 along the static housing 93. The screw-type teeth or screw lead can provide the sufficient amount of rotation to prevent recoating. After a complete coating process, sponge holder 94 can be disconnected from pusher 100 by pulling without rotation.

In another embodiment, linear and rotational movements can be combined by controlling the linear motion pusher 100 and, thereby, the linear motion of sponge holder 94 into static housing 93. This can be achieved by translating the linear motion of pusher 100 via a screw into a turning motion of sponge holder 94 and rotor 91. In this, as well as the previous embodiment the motion of sponge holder 94, catheter holder 96, rotor 91, and pusher 100 can be manually and/or mechanically activated and/or controlled.

Figure 11:
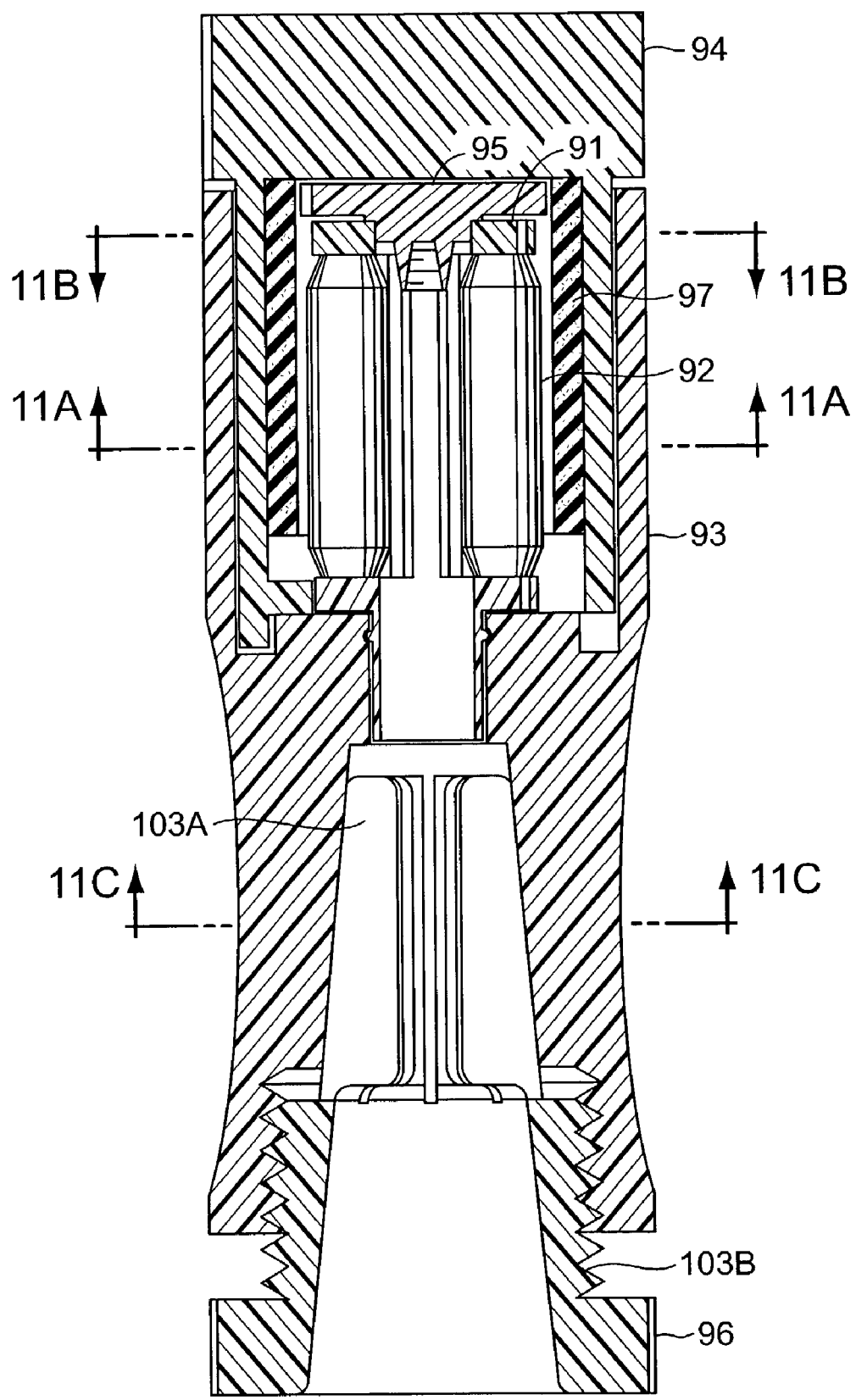
FIG. 11 illustrates a schematic of a prosthesis coating device with a roller embodiment for an applicator.
Figure 11A:
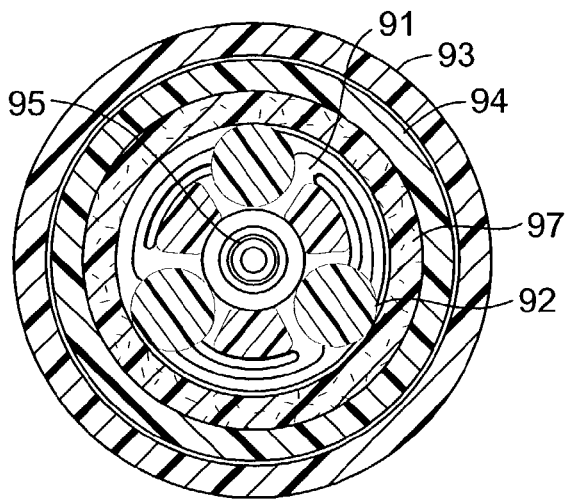
FIGS. 11A–11C illustrate different cross-sectional views of the prosthesis coating device.
Figure 11B:
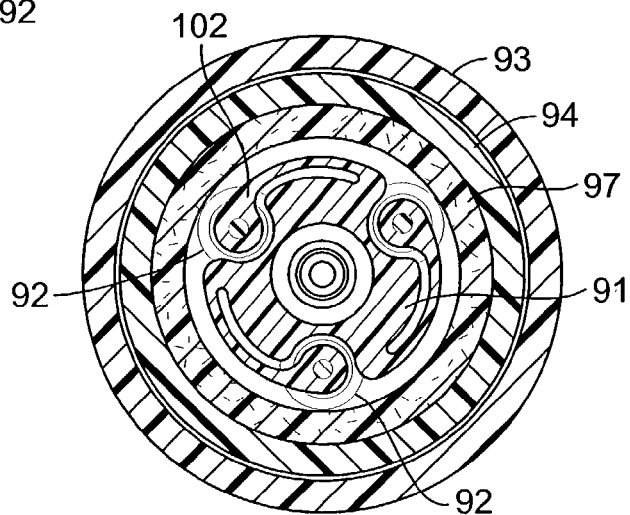
Figure 11C:
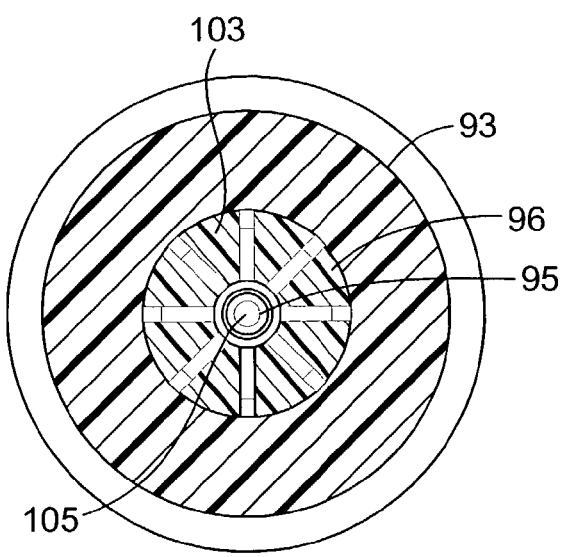

FIG. 11 illustrates another embodiment of the catheter coating device which shows sponge holder 94 and sponge cartridge 97. Rotor cap 95 is positioned within sponge holder 94 and above rollers 92. Sponge holder 94 is positioned within static housing 93. Catheter holder 96 is positioned within static housing 93. Catheter holder 96 has threads 103B to screw or ratchet into static housing 93. FIG. 11B illustrates a cross-sectional view looking downward based on FIG. 11 at plane 11B. Rotor 91 with elastic arms 102 sits on rollers 92 which contact a cylindrical sponge cartridge 97 within sponge holder 94 within static housing 93. FIG. 11A illustrates a cross-sectional view looking upward based on FIG. 11 at plane 11A. Rollers 92 are positioned below rotor 91 and radially closer to the center sponge cartridge 97, sponge holder 94, and static housing 93. FIG. 11C illustrates a cross-sectional view looking upward based on FIG. 11 at plane 11C. Catheter holder 96 has radial members that hold the catheter in place while the prosthesis is being coated while both are positioned in the static housing 93. The catheter is held straight between the radial members 103A of the catheter holder 96 and the rotor cap 95.

Figure 12:
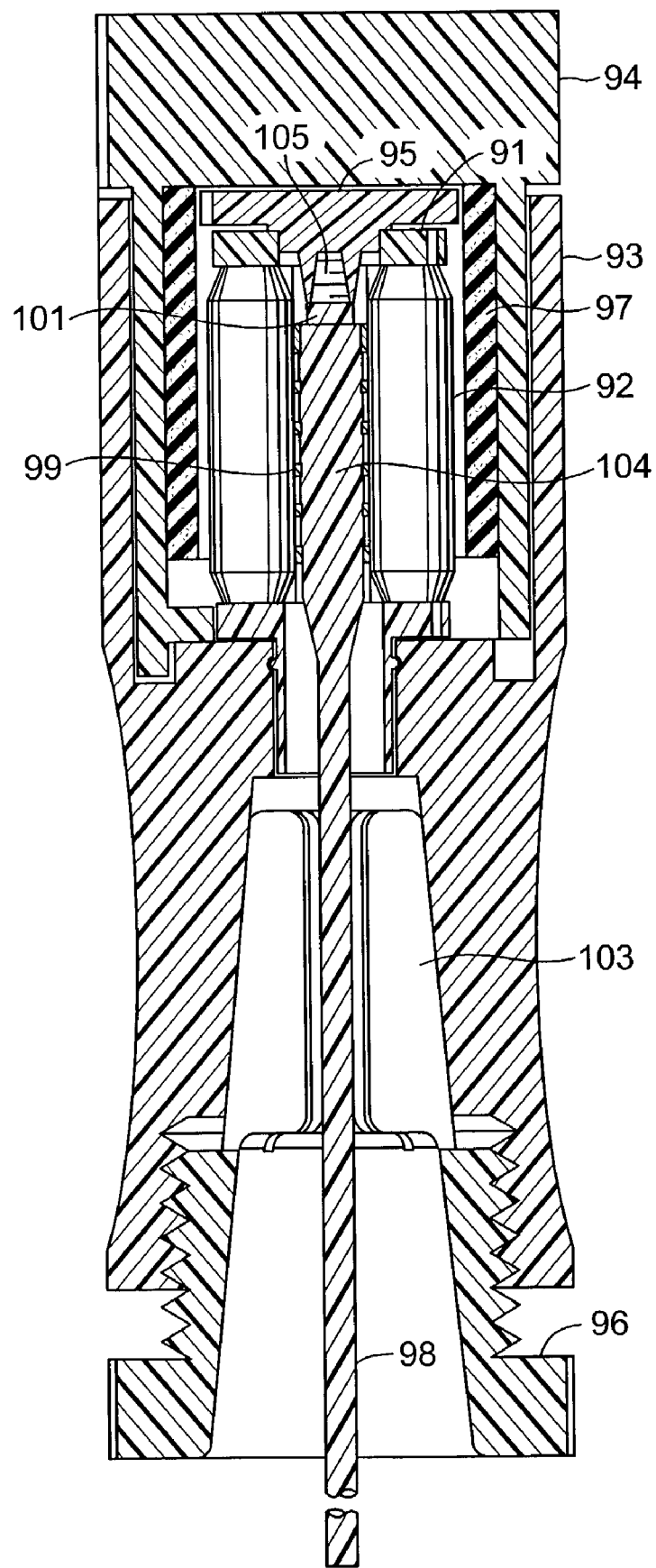
FIG. 12 illustrates a schematic of a prosthesis coating device of FIG. 11 with a stent and catheter inserted in the device.

FIG. 12 illustrates the catheter 98 and prosthesis 99 positioned within catheter holder 96 and static housing 93. The shaft of the catheter 98 is held by the radial members 103A of catheter holder 96. The catheter tip 101 is positioned to align with the cavity 105 in rotor cap 95. The catheter tip 101 can lock into cavity 105 so that rotor 91 can rotate catheter 98. Static housing 93 is static (e.g., in the hand of the operator). Sponge cartridge 97 rotates (e.g., manually by the operator) with reference to static housing 93. The balloon portion 104 of catheter 98 holds prosthesis 99, in this example, a stent. Rollers 92 align with the prosthesis 99 and sponge cartridge 97. Rollers 92 contact prosthesis 99 without contacting balloon portion 104.

In another non-limiting embodiment, liquid or semi-liquid coating materials can be applied to a prosthesis using a tampon apparatus and method. One of the advantages of the tampon are the ability to move over large area of the prosthesis while contacting with the tampon at only certain desired locations to step over large areas where no coating material is going to be applied. The tampon movement provides linear movement to contact the surface of the prosthesis on the upstroke and to absorb coating material on the down stroke and avoids applying shocking forces while contacting the prosthesis such that the coating material adheres to the prosthesis. A tampon can be constructed of silicon, PVC, urethane, chloroprene, etc. The shape of the tampon front end is designed to fit the coating application. The tampon provides control over the thickness of coating material applied to the prosthesis via the interaction of tampon and the prosthesis. The interaction of coating material delivery to the prosthesis is a function of the prosthesis surface material and surface quality, tampon material end surface quality, coating material properties like density, viscosity, surface tension, and its reaction with tampon and stent material. The tampon approaches perpendicularly flat surfaces of the prosthesis and radially curved surfaces of the prosthesis providing a precise area of contact. The tampon provides the ability to better accommodate irregular surfaces on the prosthesis. In one embodiment, the tampon can be more local than the roller so it can accommodate with local irregularities, whereas the roller touches all the stent length, the tampon can come into contact with small portions of the prosthesis.

Figure 2:
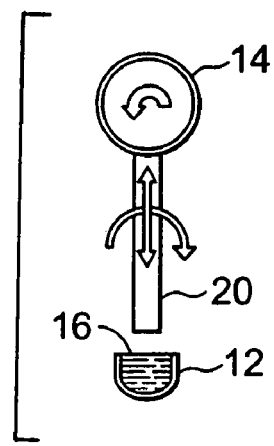
FIG. 2 illustrates a tampon embodiment for an applicator with a coating material tray.

FIG. 2 illustrates a tampon 20 which moves linearly up and down in the direction of the vertical double arrow, and rotates end-over-end clockwise. As tampon 20 moves down, the surface of tampon 20 proximate to the reservoir 12 absorbs coating material 16. Rotation of the tampon 20 makes the surface which absorbed coating material 16 from reservoir 12 distal to the reservoir 12 and proximate to the prosthesis 14. The tampon 20 then moves up to contact the prosthesis 14. As the tampon 20 rotates clockwise, the prosthesis 14 rotates counter-clockwise so that the tampon 20 can contact the portions of the surface of prosthesis 14 which are desired to be coated.

Figure 6:
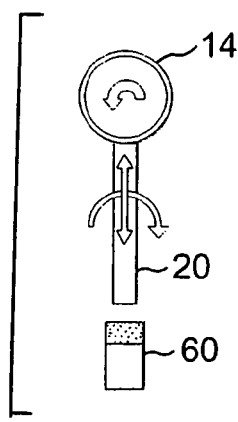
FIG. 6 illustrates a tampon embodiment for an applicator with a sponge cartridge of coating material.
Figure 7:
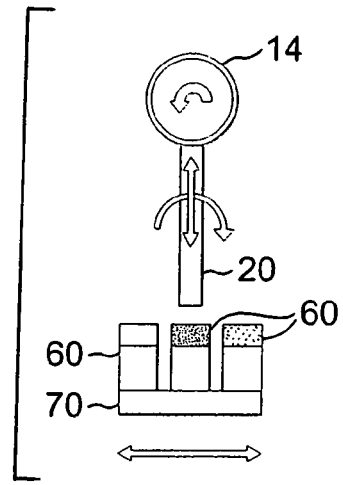
FIG. 7 illustrates a tampon embodiment for applicator with multiple sponge cartridges with different coating materials.

In other embodiments, the tampon can be used in conjunction with a sponge cartridge soaked with the coating material. In principle there is a sponge soaked with the coating material. The tampon contacts the sponge to transfer the coating material to the tampon. FIG. 6 illustrates an embodiment of a tampon 20 with a sponge cartridge 60 used to apply coating material to prosthesis 14 by a method similar to FIG. 2. In one example, several sponge cartridges can be used in a multi-stage sequence to apply different coating materials. In one embodiment, coating stages can include different coating materials such as primer coating, polymer coating and drug coating. FIG. 7 illustrates an embodiment of a tampon 20 with several sponge cartridges 60 on a tray 70. Tray 70 can be moved laterally to position tampon 20 such that it contacts different sponge cartridges 60. This can be done in sequence, e.g., in one direction, or by alternating directions.

Figure 4:
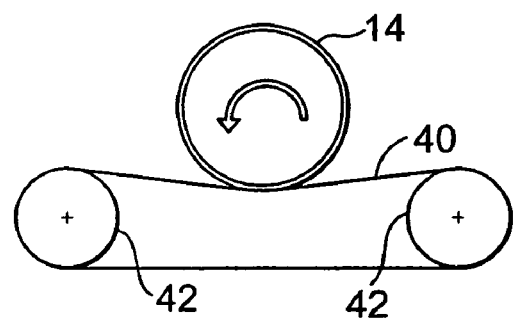
FIG. 4 illustrates a ribbon embodiment for an applicator.

In another non-limiting embodiment, a ribbon stretched between two rollers can be used to provide a flexible surface which conforms to the prosthesis to apply coating material. Other means of contouring a flexible flat surface over the prosthesis are known in the art of contact printing. The contact between the rollers and the prosthesis is line contact while the use of ribbon is a surface contact. In one embodiment, the ribbon has the same local radius as the prosthesis. FIG. 4 illustrates an embodiment of an applicator with ribbon 40 and rollers 42 which can rotate the ribbon 40 clockwise. Prosthesis 14 can rotate counter-clockwise. Ribbon 40 can conform to the surface of the prosthesis 14.

In one embodiment, the device for coating can be divided into a non-sterile, non-replaceable portion and a sterile replaceable portion. The non-sterile, non-replaceable section comprises user interface and processor which controls servo controller. The servo controller controls prosthesis stabilizer and motion driver, coating material changer, and roller or tampon driver. The sterile replaceable portion comprises prosthesis clamp, coating material reservoirs, and roller sub-assemblies or tampon. In one example, both portions can be mounted on a single base. The prosthesis stabilizer and motion driver drives the prosthesis clamp, the coating material changer drives the coating material reservoirs, and the roller or tampon driver drives the roller sub-assemblies or tampon. In one embodiment, the interfaces are both electrical and mechanical.

Figure 8:
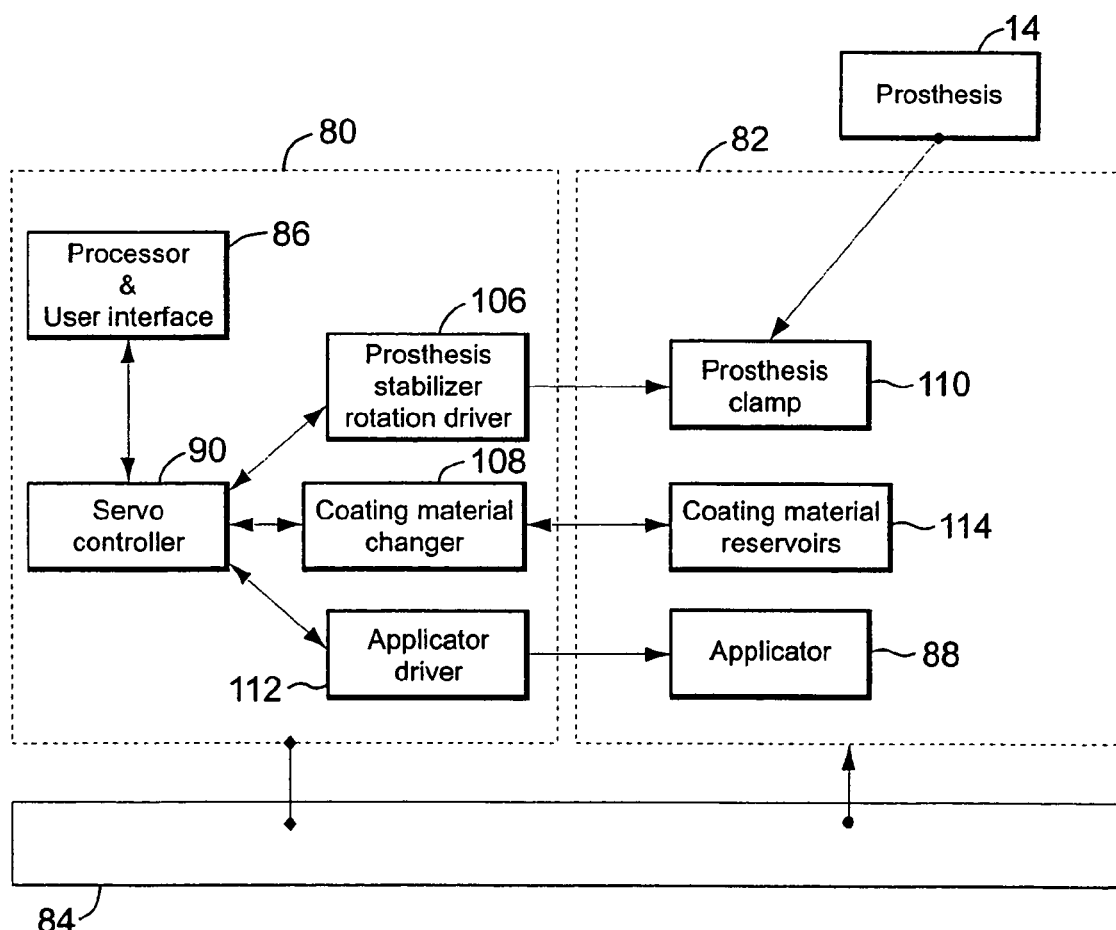
FIG. 8 illustrates a block diagram of a prosthesis coating device with a non-sterile non-replaceable section and a sterile replaceable section.

FIG. 8 is a block diagram of an embodiment of the prosthesis coating device of the present invention showing a non-sterile non-replaceable section 80 and a sterile replaceable section 82. Section 80 is permanently mounted on base 84 and section 82 is removably mounted on base 84. Section 80 comprises a processor and user interface 86. In one embodiment, the user interface is a man-machine interface or MMI which can include software and manual/mechanical interface. Servo controller 90 activates prosthesis stabilizer and rotation driver 106, coating material changer 108, applicator driver 112. An example of a coating material changer is tray 70 in FIG. 7. Prosthesis stabilizer and rotation driver 106 drives the prosthesis clamp 110 which holds prosthesis 14. An example of a prosthesis clamp is cavity 105 in FIG. 12. Coating material changer 108 drives coating material reservoirs 114. An example of coating material reservoirs are sponge cartridges 60 in FIG. 7. Applicator driver 112 drives applicator 88.

Figure 13:
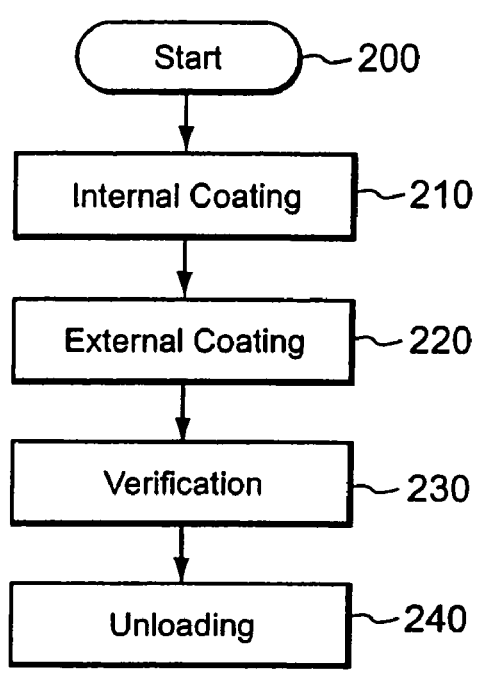
FIG. 13 illustrates a flow chart of a method of internal and external coating.
Figure 14:
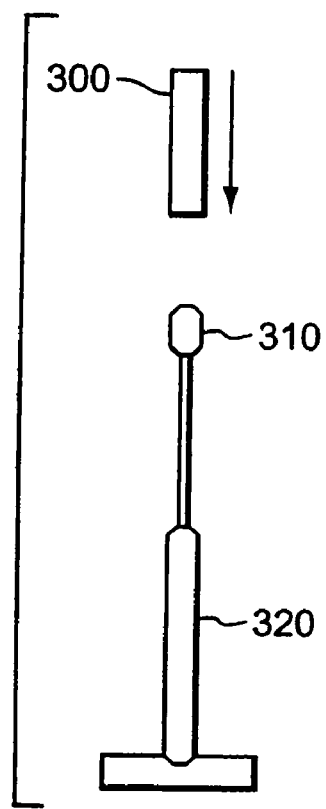
FIG. 14 illustrates a schematic of an internal applicator and mounting for an external coating.

FIG. 13 illustrates a flow chart for a method for a two stage coating process for a stent. FIG. 14 illustrates a device for internal and external coating. The process begins at start 200 by gripping the stent 300 (not shown) and driving it in the direction of the arrow over the internal coating head 310. The internal coating step 210 coats the interior surface of the stent by continuing the movement of the stent 300 in the direction of the arrow over the internal coating head 310. The interior surface refers to the surface that contacts the balloon catheter prior to insertion into the body and is exposed to the blood flow after expansion and contraction of the balloon catheter after insertion into the body. The stent 300 is then positioned on the external-coating mounting 320. The external coating step 220 coats the exterior surface of the stent 300 according to the roller and tampon embodiments described above. The exterior surface refers to the surface that is covered by the exterior lumen of a dual lumen catheter prior to insertion into the body and is in contact with the interior surface of the blood vessel after expansion of the balloon catheter after insertion into the body. The verification step 230 inspects the stent 300 for coating flaws using a scanning process which is described in copending application by inventors Avraham Shekalim and Ascher Shmulewitz, Ser. No. 10/210,714, entitled "STENT COATING DEVICE," filed on Jul. 30, 2002, which is hereby incorporated in its entirety herein by reference and is commonly owned by the same assignee of this application. The unloading step 240 removes the stent 300 from the external-coating mounting 320.

Figure 15:
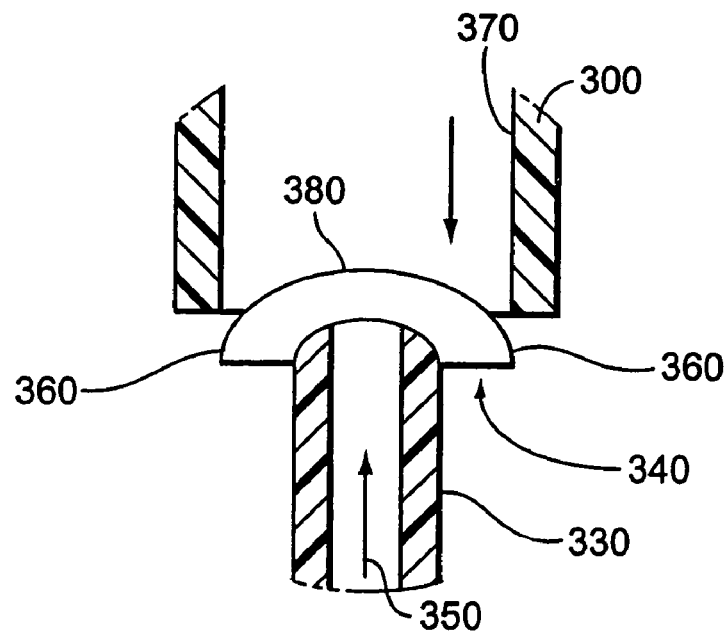
FIG. 15 illustrates a magnified view of the stent in reference to the internal applicator.

FIG. 15 illustrates a magnified stent coating device for coating the interior surface of a stent. Stent 300 is translated over internal coating head 310. Internal coating head 310 comprises an internal coating cup 340 which can be made of any synthetic material such as rubber or silicone adapted to evenly distribute the coating material on its surface. The coating material 350 flows up cup support pipe 330 to internal coating cup 340 where the coating material flows evenly over the top surface 380 of the internal coating cup 340 to its edges 360 which contact the interior surface 370 of the stent 300.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for applying a coating, comprising:
   a substantially cylindrical housing having an interior portion;

a rotor cap disposed in the interior portion of the housing, the rotor cap comprising a central axis portion and at least one roller arranaed around the central axis portion of the rotor cap; and a sponge holder capable of being disposed in the interior portion of the housing, the sponge holder having a cavity to receive the rotor cap, wherein the at least one roller is mounted on at least one elastic arm that urges the at least one roller away from the central axis portion.

2. The apparatus as recited in claim 1, wherein the sponge holder further comprises:

a sponge cartridge to carry a coating material.

3. The apparatus as recited in claim 2, further comprising:

a pusher to position the sponge holder within the housing so as to receive the rotor cap.

4. The apparatus as recited in claim 3, wherein:

the sponge cartridge contacts the at least one roller when the rotor cap is positioned within the cavity of the sponge holder.

5. The apparatus as recited in claim 4, wherein:

the at least one roller is urged toward the central axis portion when the rotor cap is positioned within the cavity of the sponge holder.

6. The apparatus as recited in claim 4, further comprising:

a stent mounted on a balloon catheter disposed in the central axis portion of the rotor cap, wherein the at least one roller is urged into contact with an exterior surface of the stent by the sponge holder.

7. An apparatus for applying a coating, comprising:

a substantially cylindrical housing having an interior portion;

a rotor cap disposed in the interior portion of the housing, the rotor cap comprising a central axis portion and at least one roller arranged around the central axis portion of the rotor cap;

a sponge holder capable of being disposed in the interior portion of the housing, the sponge holder having a cavity to receive the rotor cap, wherein the sponge holder comprises a sponge cartridge to carry a coating material; and a pusher to position the sponge holder within the housing so as to receive the rotor cap, wherein the sponge cartridge contacts the at least one roller when the rotor cap is positioned within the cavity of the sponge holder, and wherein the at least one roller is urged toward the central axis portion when the rotor cap is positioned within the cavity of the sponge holder.

8. The apparatus as recited in claim 7, further comprising:

a stent mounted on a balloon catheter disposed in the central axis portion of the rotor cap, wherein the at least one roller is urged into contact with an exterior surface of the stent by the sponge holder.

9. An apparatus for applying a coating, comprising:

a substantially cylindrical housing having an interior portion;

a rotor cap disposed in the interior portion of the housing, the rotor cap comprising a central axis portion and at least one roller arranged around the central axis portion of the rotor cap;

a sponge holder capable of being disposed in the interior portion of the housing, the sponge holder having a cavity to receive the rotor cap, wherein the sponge holder comprises a sponge cartridge to carry a coating material; and a pusher to position the sponge holder within the housing so as to receive the rotor cap;

a stent mounted on a balloon catheter disposed in the central axis portion of the rotor cap, wherein the sponge cartridge contacts the at least one roller when the rotor cap is positioned within the cavity of the sponge holder, and wherein the at least one roller is urged into contact with an exterior surface of the stent by the sponge holder.

10. The apparatus as recited in claim 9, wherein:

the at least one roller is urged toward the central axis portion when the rotor cap is positioned within the cavity of the sponge holder.

* * * * *